(12) United States Patent
Takeda et al.

(10) Patent No.: US 6,736,003 B2
(45) Date of Patent: *May 18, 2004

(54) VEHICLE PERFORMANCE EVALUATION TEST METHOD AND APPARATUS

(75) Inventors: Junichi Takeda, Oakazaki (JP); Shigeru Sakamoto, Susono (JP); Osamu Takenaka, Kariya (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 82 days.

This patent is subject to a terminal disclaimer.

(21) Appl. No.: 10/097,562

(22) Filed: Mar. 15, 2002

(65) Prior Publication Data

US 2002/0134169 A1 Sep. 26, 2002

(30) Foreign Application Priority Data

Mar. 23, 2001 (JP) ........................................ 2001-085516

(51) Int. Cl.$^7$ ................................................. G01L 5/28
(52) U.S. Cl. ................................................................. 73/132
(58) Field of Search ............................. 73/132, 121, 40, 73/126; 701/70, 76; 180/273; 60/245; 123/204.23

(56) References Cited

U.S. PATENT DOCUMENTS

| | | | | |
|---|---|---|---|---|
| 3,662,593 A | * | 5/1972 | Pirrello et al. ................. | 73/132 |
| 4,590,909 A | * | 5/1986 | Heintz .......................... | 123/360 |
| 5,430,645 A | * | 7/1995 | Keller ..................... | 364/424.01 |
| 5,821,718 A | * | 10/1998 | Shaffer et al. .............. | 318/587 |
| 6,024,420 A | * | 2/2000 | Yonemura et al. ........ | 303/113.2 |
| 6,546,327 B2 | * | 4/2003 | Hattori et al. ................. | 701/96 |

FOREIGN PATENT DOCUMENTS

| | | |
|---|---|---|
| JP | 56-169247 | 5/1980 |
| JP | A 11-132914 | 5/1999 |

* cited by examiner

Primary Examiner—Edward Lefkowitz
Assistant Examiner—Octavia Davis
(74) Attorney, Agent, or Firm—Oliff & Berridge, PLC

(57) ABSTRACT

A method and apparatus conduct a performance evaluation test for a vehicle in which an actuator that applies a depressing force to a control member to be operated by a vehicle operator is controlled by a controller. The controller controls the actuator to automatically apply the depressing force to the control member for conducting a performance evaluation test for the vehicle, and changes control of the actuator in accordance with an actual state of the vehicle.

6 Claims, 14 Drawing Sheets

VEHICLE PERFORMANCE EVALUATION TEST METHOD AND APPARATUS

INCORPORATION BY REFERENCE

The disclosure of Japanese Patent Application No. 2001-085516 filed on Mar. 23, 2001, including the specification, drawings and abstract is incorporated herein by reference in its entirety.

BACKGROUND OF THE INVENTION

1. Field of Invention

The invention relates to a vehicle performance evaluation test method and apparatus, and more particularly to a vehicle performance evaluation test method and apparatus for evaluating vehicle performance, using a pressing device that automatically applies pressure to a control member to be operated by a vehicle operator.

2. Description of Related Art

In order to conduct a test for evaluating braking performance such as a braking distance and deceleration of a vehicle, for example, a motor vehicle, a brake pedal needs to be depressed with a predetermined depressing force or the brake pedal needs to be depressed so as to achieve a predetermined deceleration while keeping the vehicle in a running state. It is, however, difficult for the vehicle operator to accurately operate the brake pedal as described above.

JP-A-11-132914 discloses a vehicle performance evaluation test apparatus that automatically operates the brake pedal for the vehicle operator. The test apparatus is fixedly set under a seat of the vehicle and is provided with a control rod which extends in a longitudinal direction of the vehicle and a driving mechanism which drives the control rod forward and backward in the longitudinal direction of the vehicle. The control rod serves to automatically operate the brake pedal with its tip such that the performance evaluation test is conducted with respect to the braking operation of the vehicle.

With the aforementioned test apparatus, the brake pedal can be automatically depressed, and therefore the vehicle operator is allowed to conduct the evaluation test for the braking operation of the vehicle without operating the brake pedal while driving the vehicle. Furthermore, since a main portion of the test apparatus is fixedly set under the seat, the possibility of interfering with the vehicle operator when he/she enters or exits the vehicle or to perform smooth driving is reduced.

In the aforementioned test apparatus, the driving mechanism is operated in accordance with a specific pattern, and accordingly, the brake pedal is depressed in accordance with a predetermined pattern. Depending on the type or state of the vehicle to be tested, the accuracy of the evaluation test may be deteriorated or the brake pedal cannot be depressed in a stable state.

SUMMARY OF THE INVENTION

It is one object of the invention to provide a performance evaluation test method for conducting the evaluation test with high accuracy irrespective of the type or state of the vehicle to be tested by depressing the control member in accordance with the actual state of the vehicle and by operating the control member in a stable state.

According to one aspect of the invention, a method of conducting a performance evaluation test for a vehicle is provided. The method is conducted by providing an actuator that applies a depressing force to a control member to be operated by a vehicle operator and a controller that controls the actuator by controlling the actuator to automatically apply the depressing force to the control member for conducting a performance evaluation test for the vehicle, and changing control of the actuator in accordance with an actual state of the vehicle. Another aspect of the invention relates to a performance evaluation test apparatus for a vehicle including an actuator that presses a control member to be operated by a vehicle operator, and a controller that controls the actuator so as to automatically press the control member for conducting a performance evaluation test for the vehicle. The controller changes control of the actuator in accordance with an actual state of the vehicle.

The control of the actuator may be varied in accordance with the actual state of the vehicle. Therefore the control member can be appropriately depressed by controlling the actuator in accordance with the actual state of the vehicle irrespective of the type of the vehicle to be tested. As a result, the evaluation test can be conducted with high accuracy irrespective of the change in the test conditions or state of the vehicle by operating the control member (e.g., a brake pedal) in a stable manner.

According to one aspect of the invention, the actual state of the vehicle is detected, and the actuator is controlled such that the vehicle is brought into a predetermined state in accordance with the detected actual state of the vehicle. The actual state of the vehicle is detected, based on which the actuator is controlled so as to bring the vehicle into a predetermined state. As the actuator can be surely and appropriately controlled in accordance with the actual state of the vehicle, the control member can be surely and appropriately depressed.

According to one aspect of the invention, the actual state of the vehicle is detected, and a parameter for the control of the actuator is changed in accordance with the detected actual state of the vehicle. The actual state of the vehicle is detected, based on which parameters for controlling the actuator are changed. Therefore the actuator can be surely and appropriately controlled in accordance with the actual state of the vehicle and the control member can be surely and appropriately depressed.

According to one aspect of the invention, the actual state of the vehicle represents a depressing force applied to the control member by the actuator. The actual state of the vehicle is represented by the depressing force applied to the control member by the actuator, and therefore the actuator is controlled in accordance with the depressing force to be applied to the control member. This makes it possible to control the depressing force applied to the control member to a desired depressing force accurately.

According to one aspect of the invention, the actual state of the vehicle represents a deceleration of the vehicle. The actual state of the vehicle is represented by deceleration of the vehicle, based on which the actuator is controlled. Hence the depressing force applied to the control member can be accurately controlled to achieve a desired deceleration of the vehicle.

According to one aspect of the invention, a running state of the vehicle is detected, and the depressing force applied to the control member is reduced by the actuator such that an evaluation test for the performance of the vehicle is stopped when it is determined that the running state of the vehicle is unstable. The running state of the vehicle is detected, and the depressing force applied to the control member is decreased to terminate the evaluation test when the running condition of the vehicle is unstable, and therefore the evaluation test can be surely prevented from being continued when the running condition of the vehicle is unstable.

According to one aspect of the invention, the control member takes form of a braking operation member, such as a pedal, for example. Since the control member takes form of the brake control member, it is possible to automatically conduct the evaluation test for braking operation of the vehicle by automatically depressing the brake control through the actuator.

Preferably, the actual state of the vehicle is varied based on which the control of the actuator changes in accordance with a type of the performance evaluation test conducted for the vehicle.

Preferably, the actual state of the vehicle represents a depressing force applied to the control member by the actuator when the performance evaluation test is conducted at a constant depressing force, and the actual state of the vehicle represents a deceleration of the vehicle when the performance evaluation test is conduced at a constant deceleration.

Preferably, a deviation between the predetermined state and the detected actual state of the vehicle is calculated, and the actuator is controlled so as to reduce the calculated deviation.

Preferably, the parameter for the control of the actuator represents a feedback control amount based on a deviation between the predetermined state and the detected actual state of the vehicle.

Preferably, the actuator is controlled by a feed-forward control amount obtained on the basis of the predetermined state of the vehicle, and then by the feed-forward control amount obtained on the basis of the predetermined state of the vehicle, and a feedback control amount on the basis of a deviation between the predetermined state and the detected actual state of the vehicle.

Preferably, the feedback control amount includes a proportional control amount and an integral control amount.

Preferably, the actuator is controlled by a feed-forward control amount obtained on the basis of the predetermined state of the vehicle, then by the feed-forward control amount and a proportional control amount of a feedback control obtained on the basis of a deviation between the predetermined state and the detected actual state of the vehicle, and subsequently by the feed-forward control amount obtained on the basis of the predetermined state of the vehicle, and the proportional control amount and an integral control amount of the feedback control obtained on the basis of the deviation between the predetermined state and the detected actual state of the vehicle.

Preferably, application of the depressing force to the control member is terminated upon stoppage of the vehicle.

Preferably, a yaw rate of the vehicle is detected, and it is determined whether a running state of the vehicle is unstable on the basis of the detected yaw rate of the vehicle.

BRIEF DESCRIPTION OF THE DRAWINGS

The invention will be described with reference to the following drawings in which like numerals refer to like elements and wherein.

DETAILED DESCRIPTION OF PREFERRED EMBODIMENTS

A preferred embodiment of the invention will be described in detail with reference to attached drawings.

Figure 1:
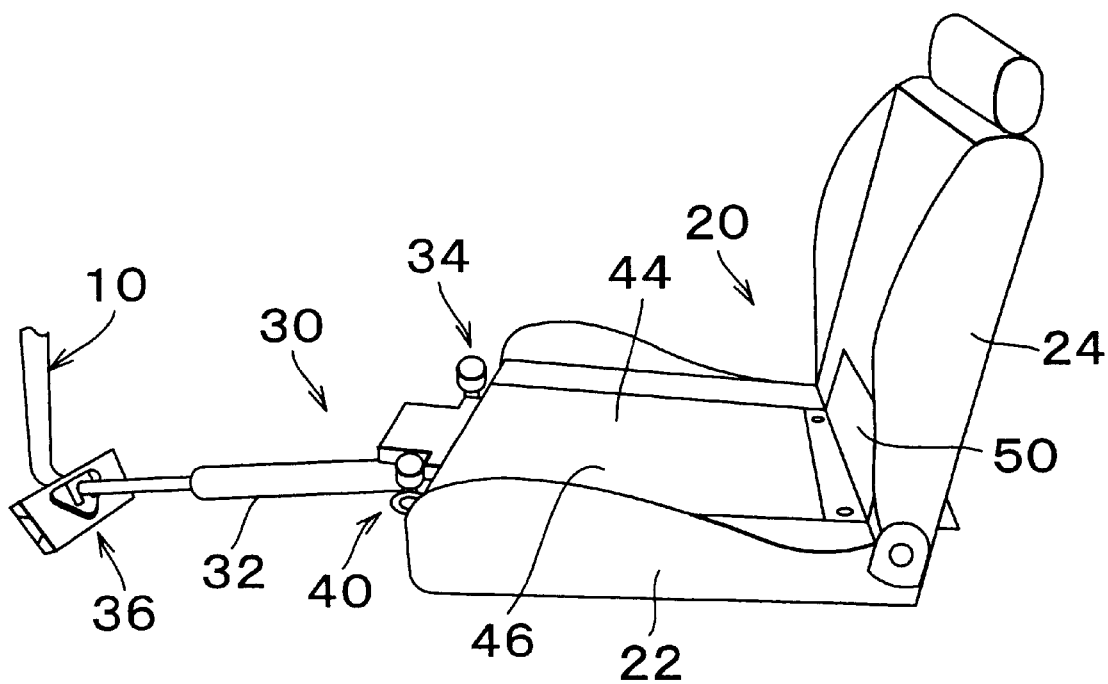
FIG. 1 is a perspective view of an actuator of a vehicle performance evaluation test apparatus according to an embodiment of the invention in a loaded state.
Figure 2:
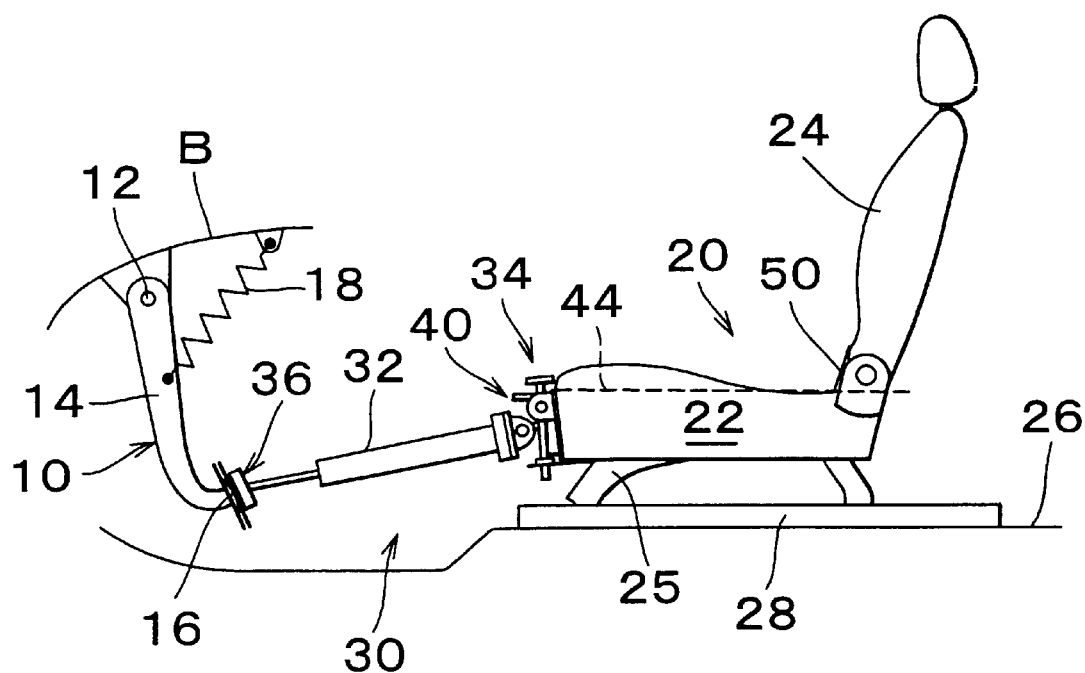
FIG. 2 is a side view of the actuator as shown in FIG. 1.
Figure 3:
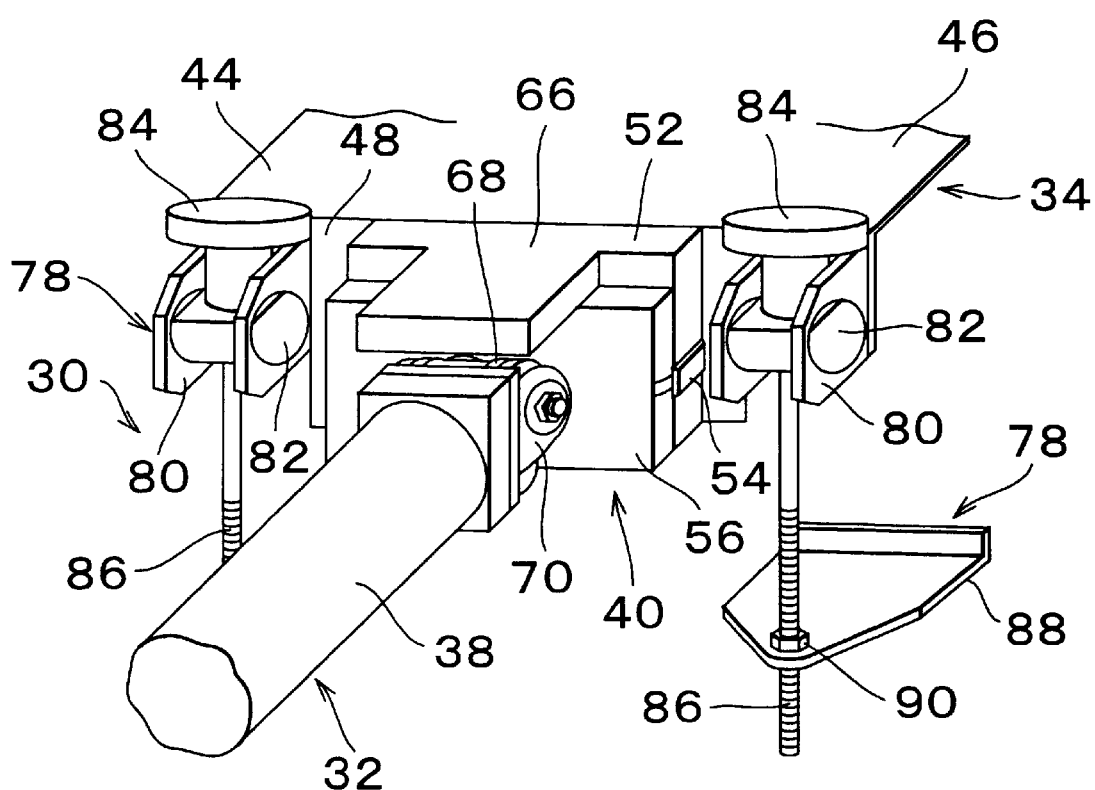
FIG. 3 is a perspective view showing a seat side fixing device of the actuator and a connecting device in a connected state.
Figure 4:
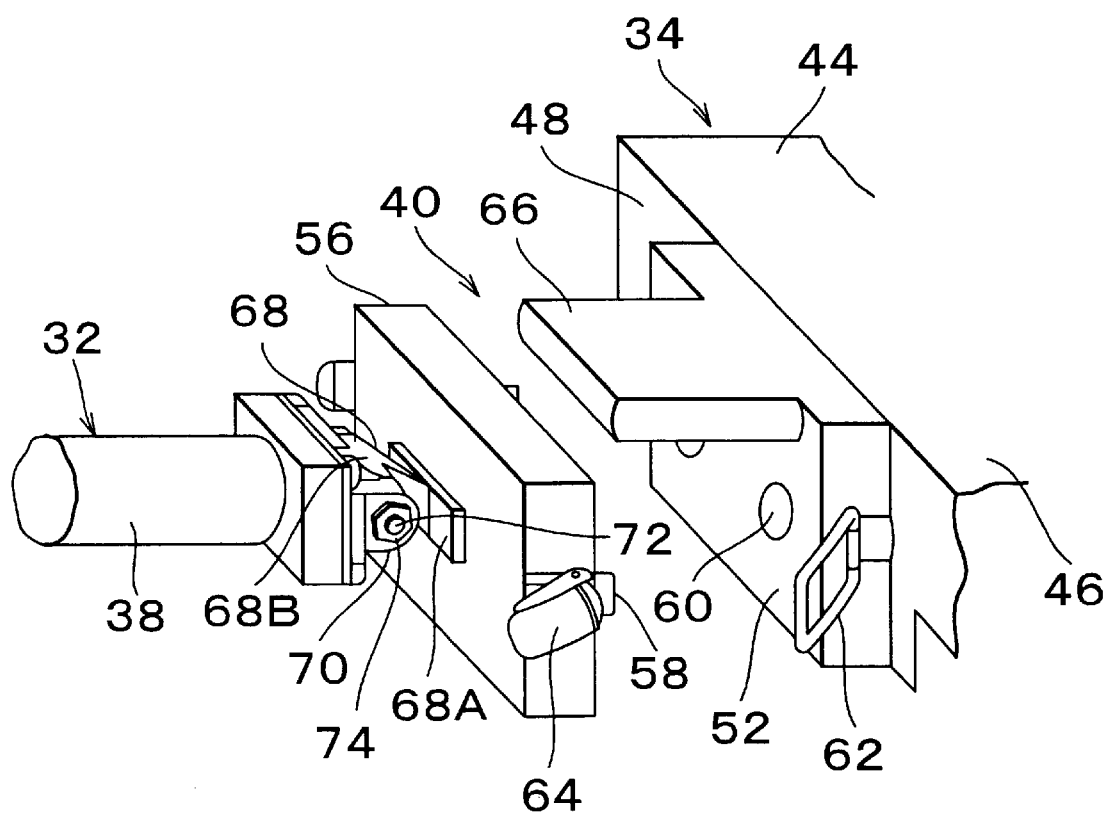
FIG. 4 is a perspective view of the connecting device of the actuator in a separated state.
Figure 5:
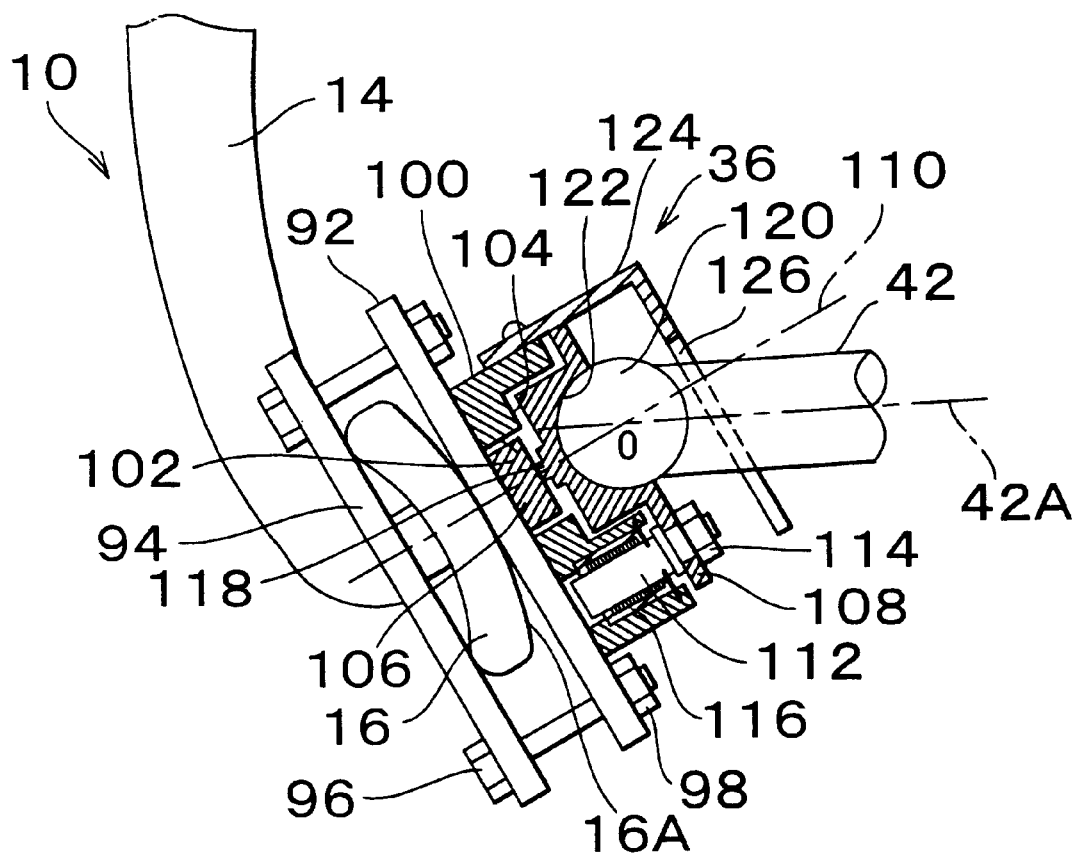
FIG. 5 is a section view of a pedal-side fixing device of the actuator.
Figure 6:
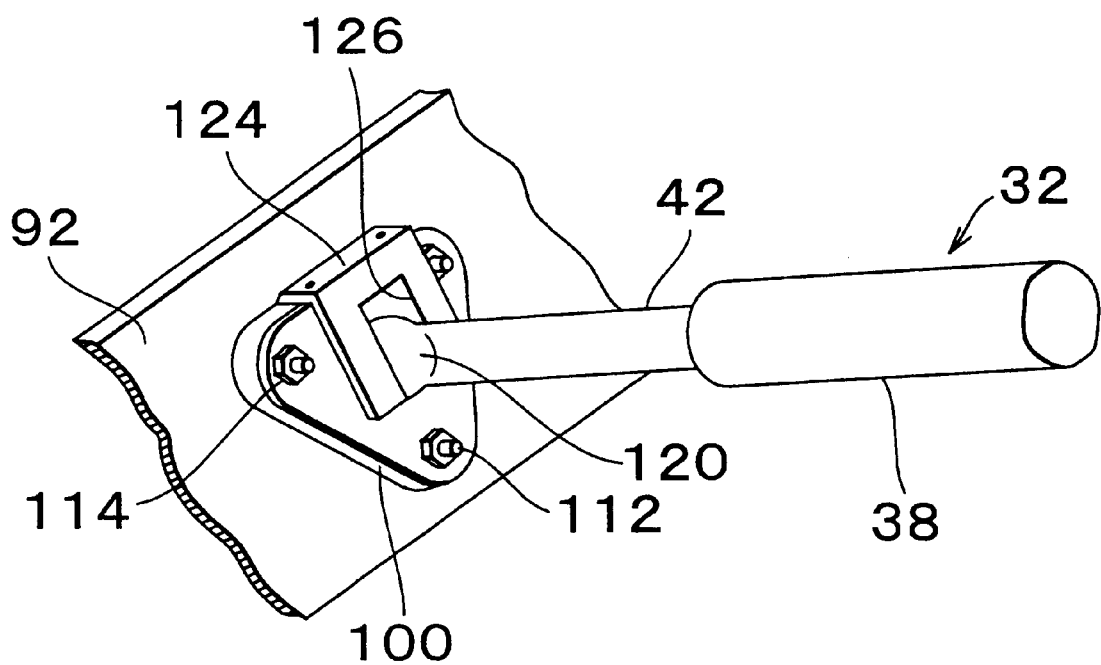
FIG. 6 is a perspective view of a main portion of the pedal-side fixing device of the actuator.
Figure 7:
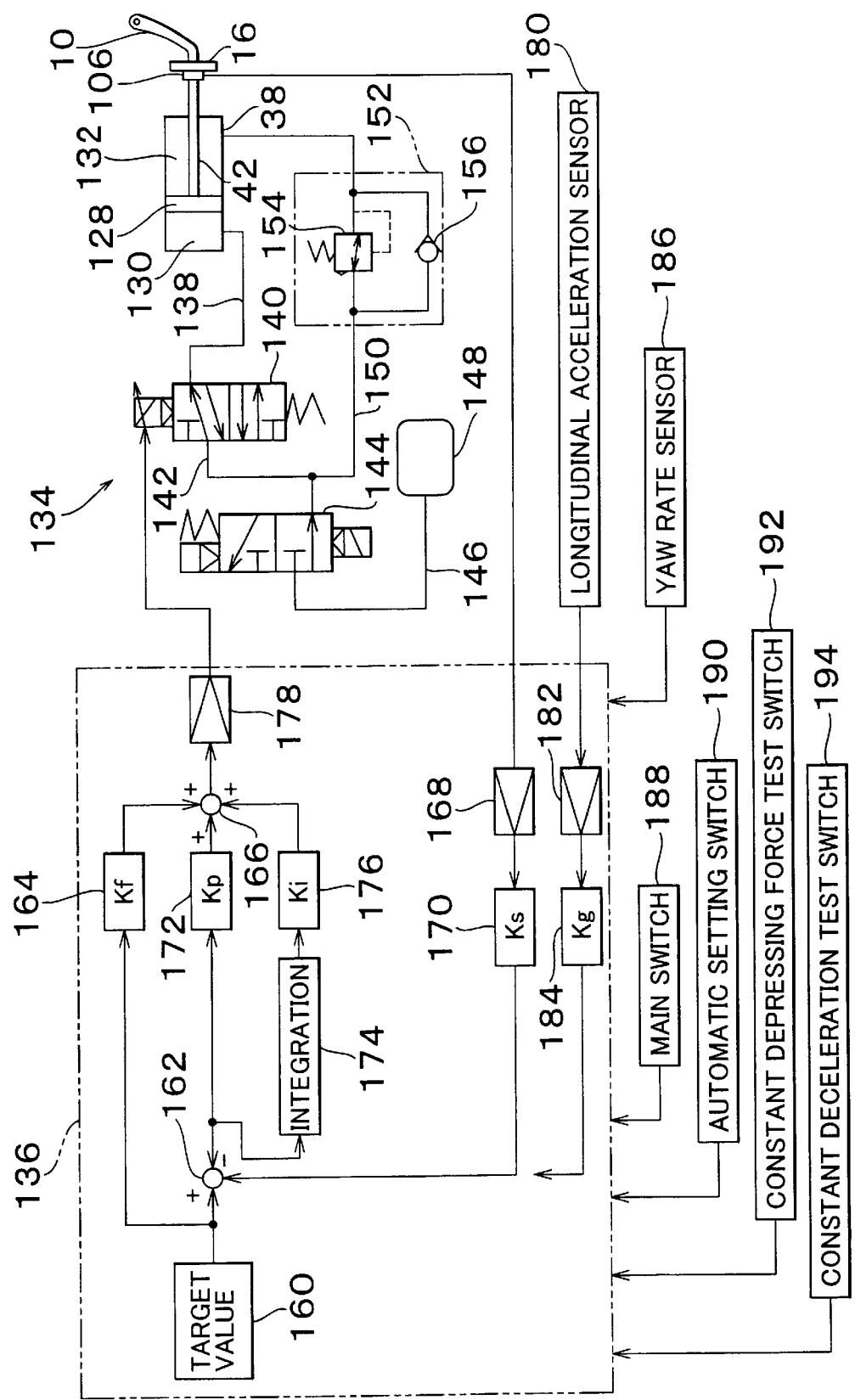
FIG. 7 is a diagram showing a pneumatic circuit and an electronic control unit for driving a pneumatic cylinder/piston device.

FIG. 1 is a perspective view of a pressing device (i.e., an actuator) of a vehicle performance evaluation test apparatus according to a preferred embodiment of the invention when the apparatus is installed in a vehicle. FIG. 2 is a side view of the pressing device as shown in FIG. 1. FIG. 3 is a perspective view showing a seat side fixing device of the pressing device and a connecting device in a connected state. FIG. 4 is a perspective view of the connecting device of the pressing device in a separated state. FIG. 5 is a section view of a pedal-side fixing device of the pressing device. FIG. 6 is a perspective view of a main portion of the pedal-side fixing device of the pressing device. FIG. 7 is a diagram showing a pneumatic circuit and an electronic control unit for driving a pneumatic cylinder/piston device.

In these figures, a brake pedal 10 serving as a control member normally is operated by a vehicle operator (not shown). Generally the brake pedal 10 is provided with an arm 14 supported by a vehicle body B via a pivot pin 12 at an upper end thereof such that the arm 14 can pivotally move in a longitudinal direction of the vehicle, and a laterally extending pedal portion 16 integrally fixed at a lower end of the arm 14. The brake pedal 10 is pivotally biased to a normal position by a return spring 18 disposed between the arm 14 and the vehicle body B.

Referring to the drawings, a seat 20 on which the vehicle operator is seated includes a seat body 22 and a seat back 24 pivotally supported at a rear end of the seat body 22 by a lower end thereof, and a plurality of legs 25 are fixed to the seat body 22. Each leg 25 engages with a seat rail 28 so as to be allowed to move in the longitudinal direction of the vehicle and is fixed on the seat rail 28 by a stopper (not shown). The rails 28 are fixed to the floor 26 of the vehicle.

One end of a pressing device (the actuator) 30 is fixed at the seat 20 and the other end of the pressing device 30 is engaged with the pedal portion 16 of the brake pedal 10. The pressing device 30 includes a pneumatic cylinder/piston device 32 which is disposed in the longitudinal direction of the vehicle and serves as a depressing force generating device, a seat-side fixing device 34, and a pedal-side fixing device 36. A cylinder 38 of the pneumatic cylinder/piston device 32 is detachably connected to the seat-side fixing device 34 through a connecting device 40. The pedal-side fixing device 36 is attached at a tip of a piston rod 42 of the pneumatic cylinder/piston device 32.

The seat-side fixing device 34 is provided with a seat engaging plate 44 having an L-like shape cross section. The seat engaging plate 44 includes a horizontal portion 46 to be located above the seat body 22 and a vertical portion 48 which abuts on a front end face of the seat body 22. A seat back abutting plate 50 is fixed to the horizontal portion 46 by welding or the like. A part of the horizontal portion 46 to the rear of the seat back abutting plate 50 is inserted between the seat body 22 and the seat back 24.

In the embodiment, the seat back abutting plate 50 is fixed to the horizontal portion 46 such that the vertical portion 48 abuts on the front end face of the seat body 22 when the rear part of the horizontal portion 46 is inserted between the seat body 22 and the seat back 24 until the seat back abutting plate 50 abuts on the seat back 24. The seat back abutting plate 50 may be attached to the horizontal portion 46 using, for example, a combination of a slot and a bolt so that the position of the seat back abutting plate 50 can be longitudinally adjusted.

As shown in FIGS. 3 and 4, a connecting device 40 is provided with a connecting board 52 fixed at a center part of the vertical portion 48 of the seat engaging plate 44 by welding or the like, and a connected board 56 to be detachably fixed to the connecting board 52 using a pair of hook assemblies 54. In this embodiment, the connected board 56 includes a pair of pins 58 and is positioned with respect to the connecting board 52 by fitting the pins 58 into corresponding pin holes 60 formed in the connecting board 52.

The hook assembly 54 includes a hook ring 62 pivotally attached at a side face of the connecting board 52 and a hook lever 64 pivotally attached at a side of the connected board 56. The connected board 56 is fixed to the connecting board 52 by pivotally moving the hook assembly 54 forward in a state where the hook lever 64 is engaged with the hook ring 62. Additionally, a horizontally longitudinally extending blocking portion 66 is integrally provided at an upper edge of the connecting board 52. The blocking portion 66 prevents the pneumatic cylinder/piston device 32 and a part of the connecting device 40 from moving up to hit the vehicle operator sitting on the seat when the vehicle operator disengages the connecting device 40 by operating the hook assembly 54.

As shown in FIG. 4, a flange portion 68A of a pivotal support member 68 is welded to a surface of the board 56 opposite to the surface of the board 56 having the pin 58. The pivotal support member 68 includes a tubular portion 68B which extends in the lateral direction of the vehicle and is disposed between a pair of brackets 70 fixed at one end of a cylinder 38 of the pneumatic cylinder/piston device 32. The tubular portion 68B is connected to the bracket 70 by a bolt 72 and a nut 74 inserted through those members. The pneumatic cylinder/piston device 32 is supported around an axis defined by the bolt 72 so as to move pivotally with respect to the connected board 56 in a vertical direction.

A pair of fixed condition adjustment assemblies 78 are provided on both sides of the connecting device 40 in the lateral direction of the vehicle. Each fixed condition adjustment assembly 78 includes a bracket 80 welded on the vertical portion 48 of the seat engaging plate 44. A pivot shaft 82 extending in the lateral direction is rotatably supported to the bracket 80. A vertically extending bolt 86 having a knob 84 at its upper end is inserted through the pivot shaft 82. The bolt 86 is supported by the pivot shaft 82 so as not to rotate relative to the pivot shaft 82.

The bolt 86 extends through a front end portion of an engaging plate 88 which engages with a bottom surface of the seat body 22, and is screwed on a nut 90 welded to the front end portion of the engaging plate 88. When the bolt 86 is turned by turning the knob 84, the engaging plate 88 accordingly moves up or down depending on the turning direction of the bolt 86. Accordingly, the seat body 22 is interposed between the seat engaging plate 44 and the engaging plate 88, and a compression load applied to the seat body 22 can be applied.

As shown in FIGS. 5 and 6, the pedal-side fixing device 36 includes a pedal abutting plate 92 which abuts on a pedal surface 16A of a pedal portion 16 of the brake pedal 10, and a pair of pedal engaging plates 94 which engage with the pedal portion 16 on both sides of the arm 14 in the lateral direction of the vehicle. The pedal abutting plate 92 and the pedal engaging plates 94 are detachably fixed to the pedal portion 16 by bolts 96 inserted therethrough and nuts 98 screwed thereon. Further, the pedal abutting plate 92 is brought into abutment on a position P of the pedal surface 16A of the pedal portion 16, which is identical to the position of a shoe sole of the vehicle operator during normal braking operation when all pairs of the bolts 96 and the nuts 98 are tightened with substantially the same amount of force.

A base member 100 substantially formed in a triangular shape is welded to the surface opposite to the surface that faces the pedal engaging plate 92. Formed at a center of the base member 100 are an opening 102 and an opening 104 communicated therewith to form a concave portion (hereinafter referred to as a concave portion 104). In the opening 102, a load sensor 106 is disposed with some play and fixed to the pedal abutting plate 92 by means of adhesion or the like. In the concave portion 104, a socket member 108 is provided so as to reciprocate along an axis 110 which is perpendicular to the surface of the pedal abutting plate 92.

Flange portions of the socket member 108 are fixed with three guide pins 112 using nuts 114. The guide pins 112 are located on a circumference of the axis 110 therealong at equal intervals. The base member 100 is provided with three ball bearing units 116 for guiding corresponding guide pins 112 in the direction parallel with the axis 110. The socket member 108 is provided with a pressing member 118 which protrudes toward the load sensor 106 along the axis 110 and a hemispherical hollow portion 122 for rotatably receiving a spherical portion 120 provided at the tip of the piston rod 42 in an opposite side thereof to which the pressing member 118 is provided. A center O of the hollow portion 122 is located on the axis 110, and therefore an axis 42A which is an axis of the piston rod 42 and the axis 110 cross at the center O.

In such a construction, the depressing force generated by the pneumatic cylinder/piston device 32 is transmitted to the socket member 108 via the spherical portion 120. However, the depression force acting in the direction along the axis 110 is only transmitted to the pedal portion 16 of the brake pedal 10 via the pressing member 118, the load sensor 106, and the pedal abutting plate 92. Therefore the load sensor 106 is capable of detecting only the depression force applied to the pedal surface 16A of the pedal portion 16 in the direction along the axis 110 accurately.

Furthermore, fixed at a side face of the base member 100 is a holding plate 124 having an L-like cross section so as to prevent the spherical portion 120 from coming off the hollow portion 122. The holding plate 124 includes a substantially rectangular cut-out 126 for receiving the piston rod 42. The cut-out 126 abuts on or overhangs close to the spherical portion 120. The holding plate 124 is formed from a metal plate such as a steel plate. When a force greater than a predetermined value is applied to the spherical portion 120 in a direction where the spherical portion 120 comes off the hollow portion 122, the spherical portion 120 elastically or plastically deforms the holding plate 124 in a direction so that the holding plate 124 moves away from the base member 100. As a result, the spherical portion 120 moves away from the socket member 108 such that the piston rod 42 is disconnected from the pedal portion 16.

As schematically shown in FIG. 7, the pneumatic cylinder/piston device 32 includes a first chamber 130 and a second chamber 132 defined by a piston 128 fixed to the piston rod 42. A pressure P1 within the first chamber 130 and a pressure P2 within the second chamber 132 are controlled by a pneumatic circuit 134 and an electronic control unit 136 for increasing or decreasing the depressing force applied from the pressing device 30 to the pedal portion 16 of the brake pedal 10.

The first chamber 130 of the pneumatic cylinder/piston device 32 is connected to a first port of an electropneumatic proportional valve 140 via a pipe 138. A second port of the electropneumatic proportional valve 140 is connected to one end of a pipe 142. A first port of a master valve 144 is connected to the other end of the pipe 142. A second port of the master valve 144 is connected to an air tank 148 via a pipe 146. A pressure in the air tank 148 is controlled to a value between predetermined upper and lower limit values using an air pump or the like.

One end of a pipe 150 is connected to the pipe 142 and the other end of the pipe 150 is connected to the second chamber 132 of the pneumatic cylinder/piston device 32. Provided midway in the pipe 150 is a regulating device 152 provided with a regulator 154 for controlling a pressure at the cylinder piston device 32 side as a pilot pressure, and a check valve 156 that allows the compressed air to flow from the second chamber 132 to the pipe 142 by bypassing the regulator 154. The regulator 154 and the check valve 156 cooperate with each other to control the pressure P2 within the second chamber 132 to a substantially constant value.

When the vehicle performance evaluation test apparatus is not operated, that is, when no control signal is sent to a solenoid of the master valve 144 from the electronic control unit 136, a valve position of the master valve 144 is set at a first position as shown in FIG. 7. As a result, communication between the pipes 146 and 142 is disconnected, and the pipe 142 is opened to an ambient air. Conversely, when the control voltage is applied to the solenoid of the master valve 144 by the electronic control unit 136, the valve position of the master valve 144 is switched to a second position. As a result, the pipes 146 and 142 are communicated with each other.

On the other hand, when the vehicle performance evaluation test apparatus is not operated, that is, when no control signal is sent to a solenoid of the electropneumatic proportional valve 140 by the electronic control unit 136, the position of the electropneumatic proportional valve 140 is set at a first position. Then the first chamber 130 is opened to the ambient air via the pipe 138. Conversely, when the control voltage is applied to the solenoid of the electropneumatic proportional valve 140 by the electronic control unit 136, the valve position is switched to a second position shown in FIG. 7. As a result, the pipes 142 and 138 are communicated. A compressed air at a pressure in proportion to the applied control voltage is then supplied into the first chamber 130 of the pneumatic cylinder/piston device 32 via the pipe 138. Accordingly the pressure P1 of the first chamber 130 is controlled to be increased or decreased.

When the vehicle performance evaluation test apparatus is not operated, the pressure P1 in the first chamber 130 and the pressure P2 in the second chamber 132 of the pneumatic cylinder/piston device 32 become atmospheric pressures. Therefore a position of the piston 128 with respect to the cylinder 38 of the pneumatic cylinder/piston device 32 can be freely changed. This makes it possible to freely adjust the length of the pneumatic cylinder/piston device 32.

The electronic control unit 136 includes a target value setting unit 160 for setting a target value, for example, a target pedal depressing force Fbpt applied to the pedal portion 16 of the brake pedal 10 by the operator. An output value of the target value setting unit 160, that is, a signal indicating the target value, for example, the target pedal depressing force Fbpt is concurrently input to a positive terminal of an accumulator 162 and a gain multiplier 164 for a feed-forward control, and then is input to an adder 166 after calculation of a feed-forward gain Kf performed by the multiplier 164.

An output of the load sensor 106 installed in the pedal side fixing device 36, that is, the signal indicating the pedal depressing force Fbp applied to the pedal portion 16 of the brake pedal 10 by the pressing device 30, is sent to the gain multiplier 170 via an amplifier 168. After a gain Ks is applied through multiplication by the gain multiplier 170, the signal is input to a negative terminal of the accumulator 162. An output of the adder 162 is then input to a proportional gain multiplier 172 for feedback control. After a proportional gain Kp is applied through multiplication by the proportional gain multiplier 172, the signal is input to the adder 166.

An output value of the adder 162 is sent to an integration circuit 174, and an output of the integration circuit 174 is sent to an integral gain multiplier 176 for feedback control. After an integral gain Ki is applied through a multiplication by the integral gain multiplier 176, the signal is sent to the adder 166. An output of the adder 166 is sent to the solenoid of the electropneumatic proportional valve 140 via the amplifier 178 as a control command signal for controlling the electropneumatic proportional valve 140 to thereby control the pressure P1 within the first chamber 130 of the pneumatic cylinder/piston device 32 to be increased or decreased.

Referring to FIG. 7, the electronic control unit 136 receives a signal generated from the longitudinal acceleration sensor 180, indicating a longitudinal acceleration Gx via an amplifier 182 and a gain multiplier 184 where necessary or desirable as shown in FIG. 7. The electronic control unit 136 also receives a signal generated from a yaw rate sensor 186, indicating a yaw rate y of the vehicle via an amplifier (not shown) where necessary or desirable. The electronic control unit 136 is provided with a main switch 188, a feed-forward gain automatic setting switch 190, a constant depressing force test switch 192, and a constant deceleration test switch 194.

The electronic control unit 136 may be formed as a control device such as one constituted of a drive circuit and a general type of a computer which includes a CPU, a ROM, a RAM and input/output ports, all connected to one another via a bidirectional common bus. A calculation by the accumulator 162 and the like may be performed by a control program installed in the micro computer.

Figure 8:
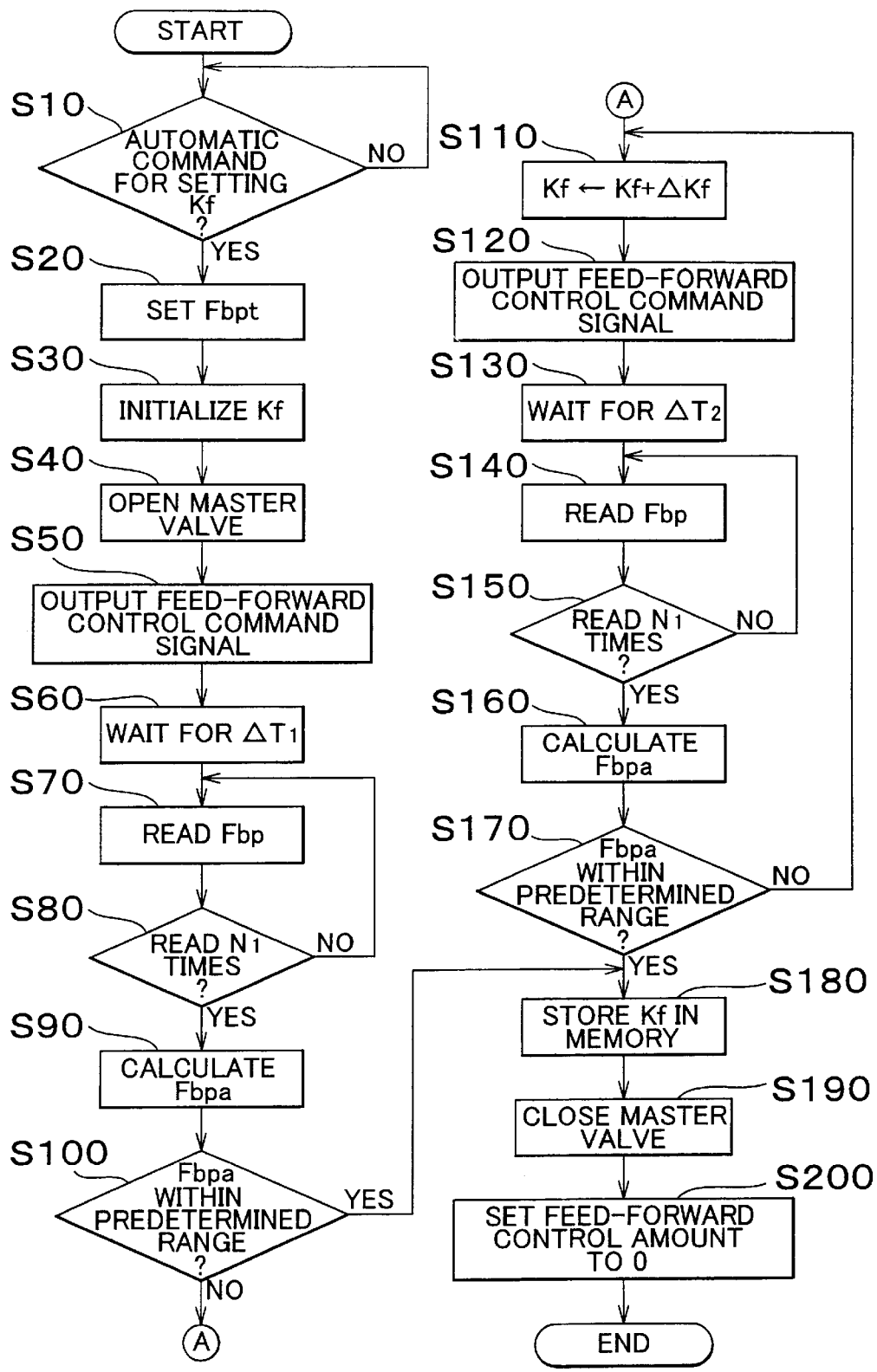
FIG. 8 is a flowchart of a control routine for automatically setting a feed-forward gain Kf in an embodiment shown in the figures.
Figure 9:
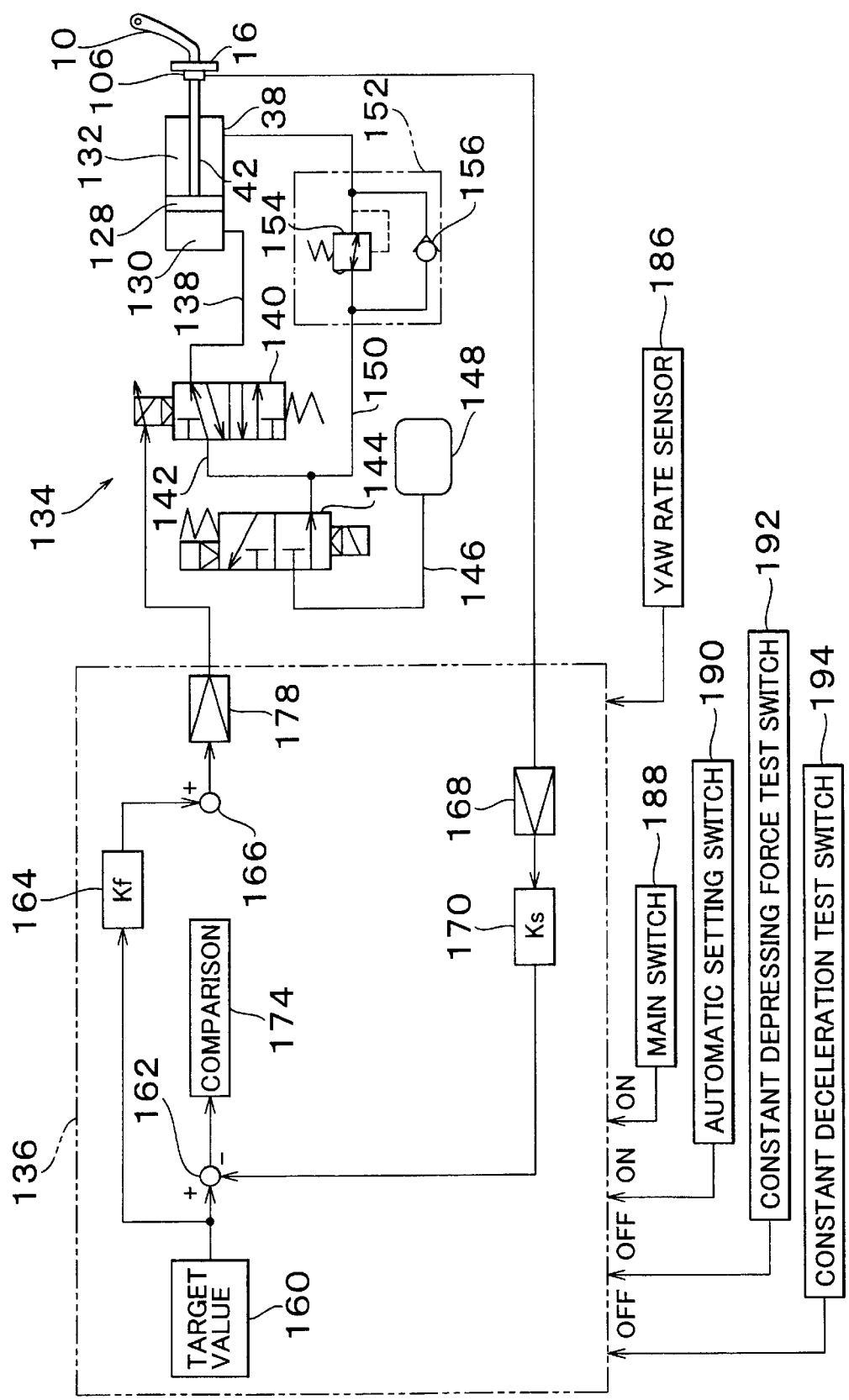
FIG. 9 is a view showing a state of the electronic control unit and the pneumatic circuit upon automatic setting of the feed-forward gain Kf.

FIG. 8 is a flowchart showing a control routine for automatically setting the feed-forward gain Kf as one of the control programs. This control is executed when the feed-forward gain automatic setting switch 190 is turned off when the main switch 188 is turned off. FIG. 9 is a schematic diagram that shows a state of the electronic control unit 136 and the pneumatic circuit 134 upon automatic setting of the feed-forward gain.

Figure 10:
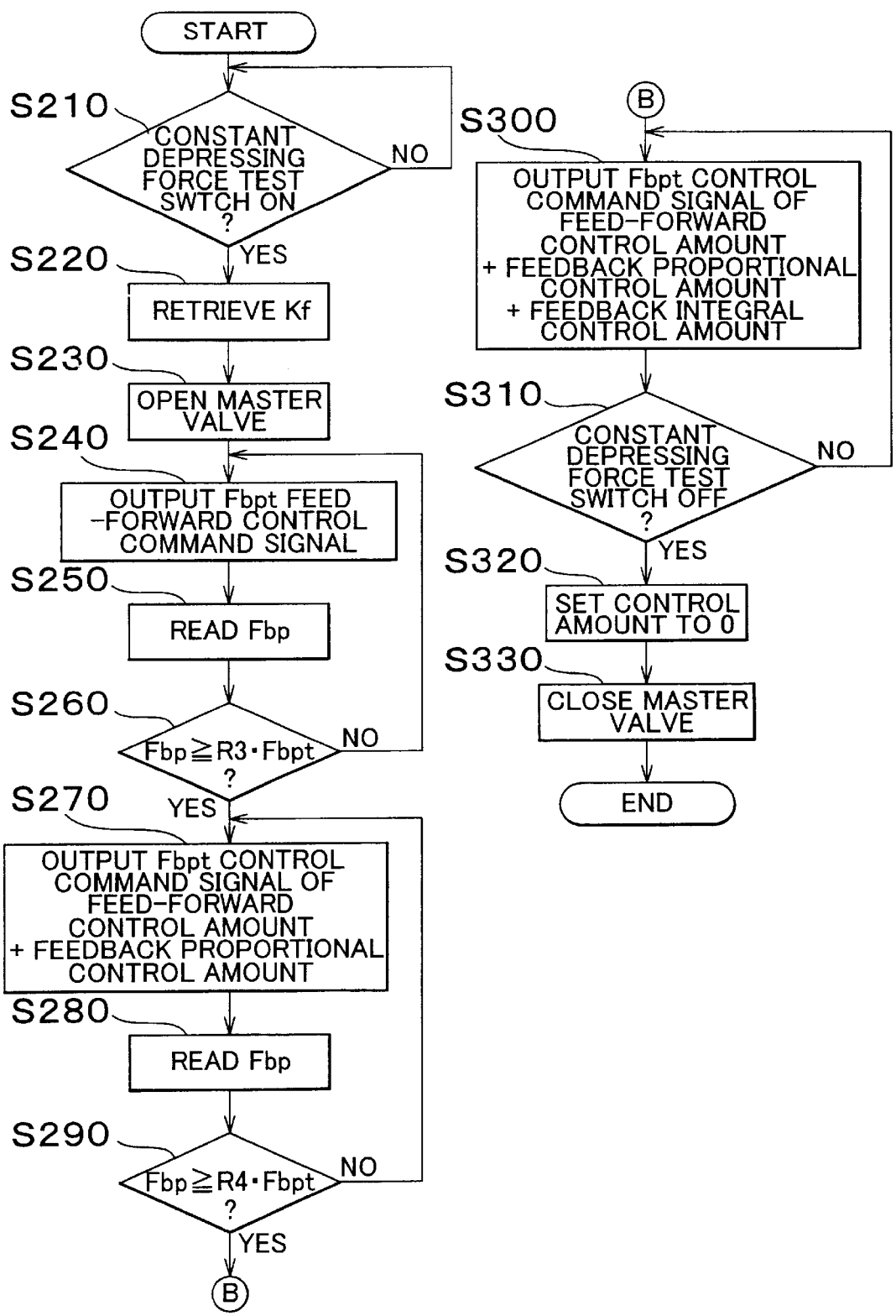
FIG. 10 is a flowchart of a control routine for a constant depressing force test according to the embodiment shown in the figures.
Figure 11:
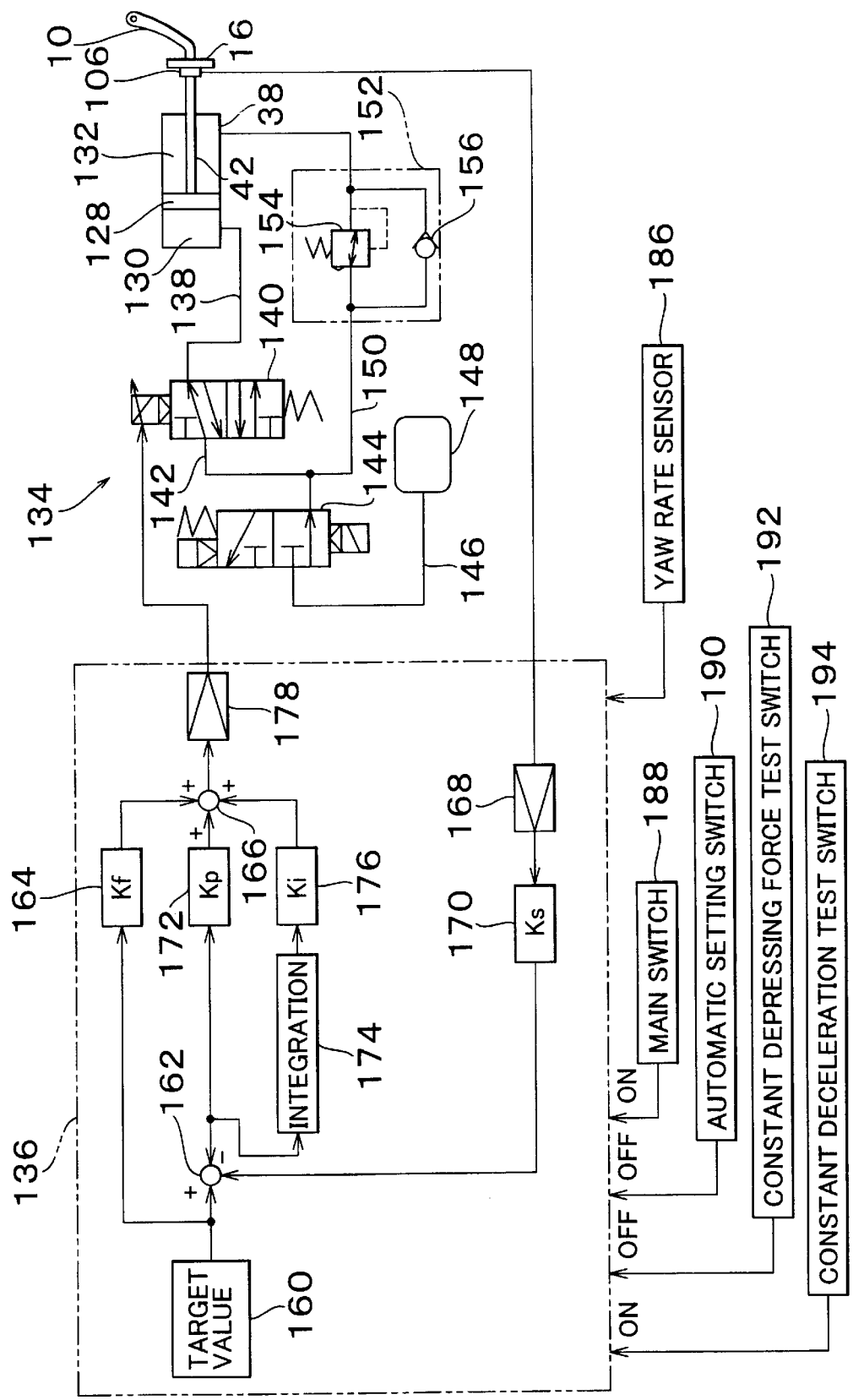
FIG. 11 is a view showing a state of the electronic control unit and the pneumatic circuit upon execution of the constant depressing force test.

FIG. 10 is a flowchart of a control routine for the constant depressing force test as one of the control programs, and this control according to the flow chart is performed when the constant depressing force test switch 192 is closed while the main switch 188 is turned on. FIG. 11 is an explanatory drawing showing a state of the electronic control unit 136 together with the pneumatic circuit 134 at the time of performing the constant depressing force test.

Figure 12:
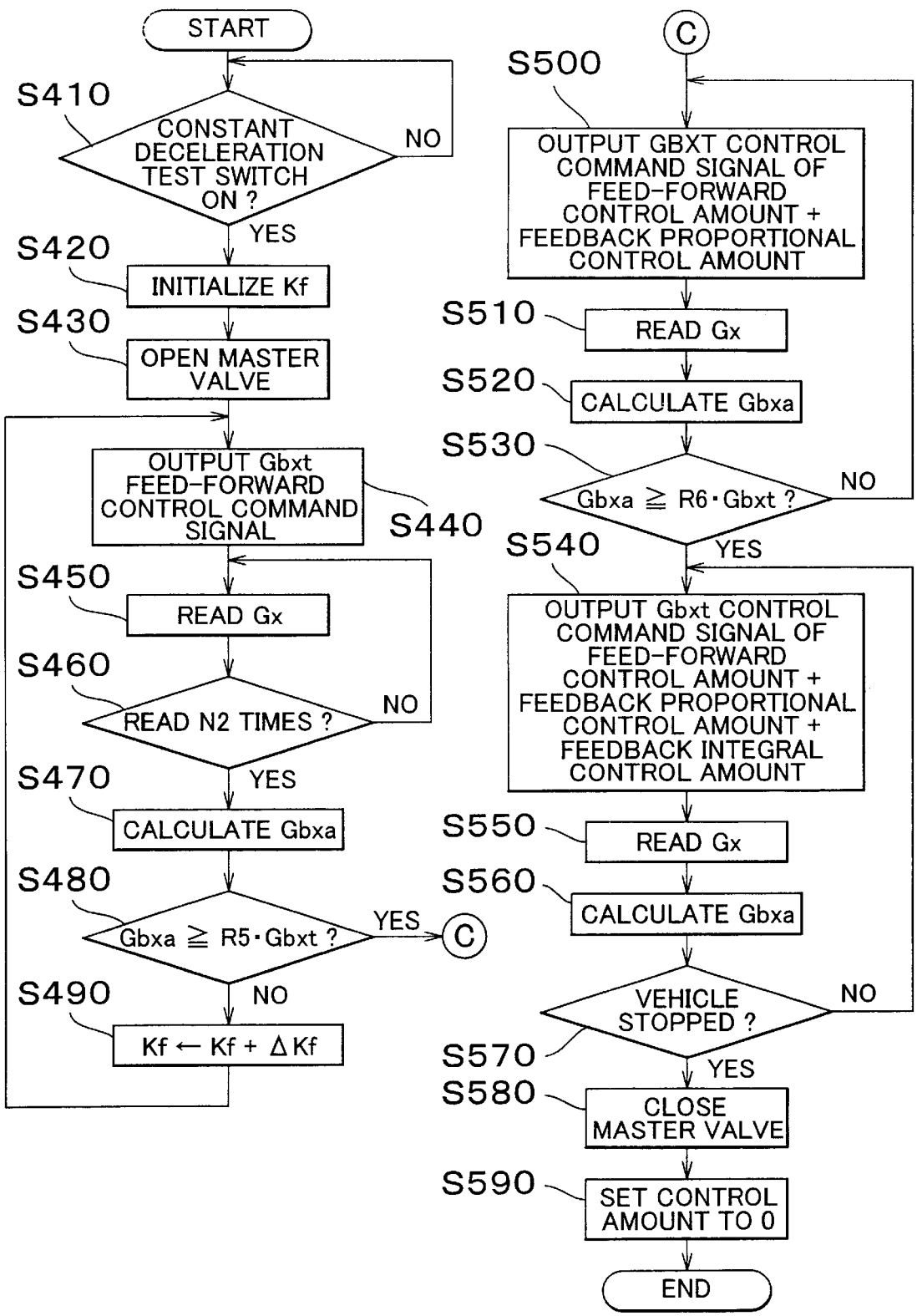
FIG. 12 is a flowchart of a control routine for a constant speed test according to the embodiment shown in the figures.
Figure 13:
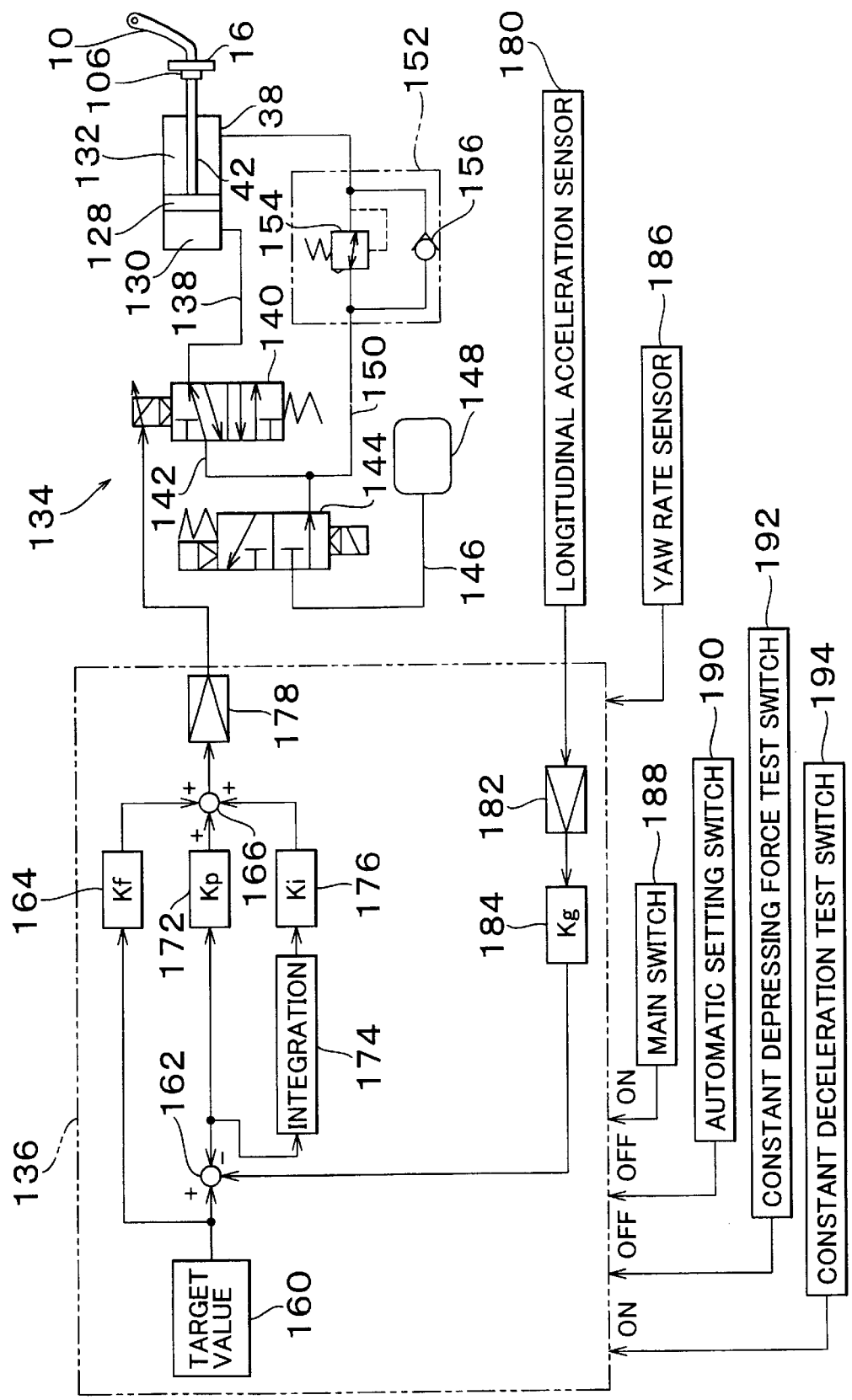
FIG. 13 is a view showing a state of the electronic control unit with the pneumatic circuit upon execution of the constant speed test.

Further, FIG. 12 is a flowchart of a control routine for conducting the constant deceleration test as one of the control programs. This control is executed when the constant deceleration test switch 194 is closed in the state where the main switch 188 is turned on. FIG. 13 is an explanatory view showing a state of the electronic control unit 136 and the pneumatic circuit 134 upon start of the constant deceleration test.

When a braking performance of the vehicle is tested for evaluation using the aforementioned vehicle performance evaluation test apparatus, the rear end of the horizontal portion 46 of the seat engaging plate 44 of the seat-side fixing device 34 is inserted between the seat body 22 of the seat 20 and the seat back 24, and the seat engaging plate 44 is positioned with respect to the seat 20 such that the seat back abutting plate 50 abuts on the seat back 24 and the vertical portion 48 abuts on a front face of the seat body 22.

Then the engaging plate 88 of the fixed condition adjustment assembly 78 is positioned underneath the seat body 22. When the knob 84 is turned in the aforementioned state, the seat body 22 is interposed under pressure between the horizontal portion 46 of the seat engaging plate 44 and the engaging plate 88 to thereby fix the seat-side fixing device 34 to the seat 20. Then the connected board 56 is connected to the connecting board 52 via the hooking assembly 54, fitting the pins 58 of the connecting device 40 into the pin holes 60. In such a manner, one end of the pneumatic cylinder/piston device 32 is fixed to the seat 20 via the connecting device 40 and the seat-side fixing device 34.

Next, the other end of the pneumatic cylinder-piston device 32 is fixed to the pedal portion 16 of the brake pedal 10 by interposing the pedal portion 16 of the brake pedal 10 under pressure between the pedal abutting plate 92 and the engaging plates 94 of the pedal-side fixing device 36, and screwing the nuts 98 on the bolts 96. Then the stopper of the seat 20 is released such that the seat 20 is moved in the longitudinal direction of the vehicle. The angle of the pneumatic cylinder/piston device 32 is then adjusted with respect to the pedal surface 16A of the pedal 16, and the seat 20 is fixed by the stopper. As pressures in the first chamber 130 and the second chamber 132 of the pneumatic cylinder/piston device 32 are both equal to the ambient pressure, the length of the pneumatic cylinder/piston device 32 freely changes as the seat 20 moves in the longitudinal direction.

The vehicle operator is seated on the seat 20 and turns the knob 84 of the fixed condition adjustment device 78 to adjust a squeezing load applied to the seat body 22 between the horizontal portion 46 of the seat engaging plate 44 and the engaging plate 88 such that the seat-side fixing device 34 is securely fixed to the seat 20. After completing the preparation for the evaluation test, the operator starts the evaluation test by operating, for example, the feed-forward gain automatic setting switch 190 of the electronic control unit 136 and the like.

Setting of Feed-Forward Gain

Referring to the flowchart shown in FIG. 8, description will be made of a procedure of the automatic setting of the feed-forward gain Kf according to one embodiment. This automatic setting control for automatically setting the feed-forward gain Kf is executed in the state where the vehicle is stopped.

In step S10, it is first determined whether the automatic setting switch 190 for setting the feed-forward gain Kf has been switched from OFF to ON by the vehicle operator. If No is obtained, the process returns to step S10 until Yes is obtained. If Yes is obtained in step S10, the process proceeds to step S20.

In step S20, the target depressing force Fbpt set upon operation of the target value setting unit 160 performed by the vehicle operator is read into a memory, and the process proceeds to step S30. In step S30, the feed-forward gain Kf is set to an initial value. This initial value is set so as to be greater than 50% of the target depressing force Fbpt but less than 100% of the target depressing force Fbpt by means of the pressing device 30.

In step S40, a control signal is output to the master valve 144 to switch the valve position thereof from the first position to the second position. In step S50, a feed-forward control command signal for achieving the target depressing force Fbpt corresponding to Fbpt-Kf, which is a product of the target depressing force Fbpt and the feed-forward gain Kf, is output to the electropneumatic proportional valve 140 to control the pressure P1 in the first chamber 130 of the pneumatic cylinder/piston device 32 for the feed-forward control. Then a waiting time $\Delta T1$ (a positive constant number), which is a time required for completing a compression control of the electropneumatic proportional valve 140, is given in step S60.

In step S70, a signal indicating the depressing force Fbp detected by the load sensor 106 is read. Next, in step S80, it is determined whether reading of the signals indicating the depressing force Fbp has been performed N1 (positive constant integer) times. If No is obtained, step S70 is repeatedly executed. On the other hand, if Yes is obtained, the process proceeds to step S90.

In step S90, an average value Fbpa, of the depressing forces Fbp detected N1 times, is calculated. In step S100, it is determined whether the average value Fbpa is within a predetermined range from R1-Fbpt to R2-Fbpt (R1, R2: positive constant values greater than 0.5 but smaller than 1

(R1<R2)). If Yes is obtained, the process proceeds to step S180. If No is obtained, the process proceeds to step S110.

In step S110, a feed-forward gain Ff is incremented by ΔKf which is a positive small constant value. Then steps S120 through S170 are executed in the same manner as steps S50 through S100. A value of awaiting time ΔT2 in step S130 is a positive constant value. It is preferable that the value ΔT2 be smaller than the waiting time ΔT1 in step S60. However, it may be equal to ΔT1. The number of times for reading the signal indicating the depressing force Fbp determined in step S150 is updated to 0 every time the feed-forward gain Ff is incremented by ΔKf in step S110.

If No is obtained in step S170, that is, if the average value Fbpa of the depressing forces Fbp detected N1 times deviates from the predetermined range, the control returns to step S110. If Yes is obtained in step S170, the process proceeds to step S180 where the feed-forward gain Kf is recorded in the memory. Then, in step S190, the valve position of the master valve 144 is returned to the first position from the second position, and thereby the first chamber 130 and the second chamber 132 of the pneumatic cylinder/piston device 32 are opened to the ambient air. In step S200, a control amount of the feed-forward control command signal is reset to 0.

Constant Depressing Force Test

Next, a procedure of the constant depressing force test according to the embodiment will be described referring to the flowchart of FIG. 10. This constant depressing force test is started in the state where the vehicle is driven by a vehicle operator at a constant vehicle speed.

In step S210, it is first determined whether the constant depressing force test switch has been switched from OFF to ON by the vehicle operator. If No is obtained, step S210 is repeatedly executed until Yes is obtained in step S210. If Yes is obtained in step S210, the process proceeds to step S220 where the feed-forward gain Kf recorded in the memory is read out. Then the valve position of the master valve 144 is switched from the first position to the second position in step S230.

In step S240, a feed-forward control command signal corresponding to a product of the target depressing force Fbpt set by the vehicle operator through operation of the target value setting unit 160 and the feed-forward gain Kf is output to the electropneumatic proportional valve 140. In step S250, the signal indicating the depressing force Fbp detected by the load sensor 106 is read. In step S260, it is determined whether the depressing force Fbp is greater than or equal to the value of R3 Fbpt (R3: a positive constant value greater than R2 but smaller than 1). If No is obtained in step S260, the process returns to step S240. Meanwhile, if Yes is obtained in step S260, the process proceeds to step S270.

In step S270, a deviation ΔFbp (=Fbpt−Fbp) between the target depressing force Fbpt and the depressing force Fbp is calculated, and a control command signal corresponding to a sum of a feed-forward control amount Fbpt·Kf for the constant depressing force test and a proportional control amount ΔFbpt·Kf for the feedback control is output to the electropneumatic proportional valve 140. In such a manner, a control of the depressing force applied to the pressing device 30 is changed to a feedback control from an open control in step S270.

In step S280, the signal indicating the depressing force Fbp detected by the load sensor 106 is read. Then in step S290, it is determined whether the depressing force Fbp is greater than or equal to R4·Fbpt (R4: positive constant greater than R3 but smaller than 1). If No is obtained in step S290, the process returns to step S270. Meanwhile, if Yes is obtained, the process proceeds to step S300.

In step S300, the deviation ΔFbp (=Fbp−Fbpt) between the target depressing force Fbpt and the depressing force Fbp is calculated and a control command signal corresponding to a sum of the target depressing force Fbpt and an integral control amount Fbpt·K1 for the feedback control is output to the electropneumatic proportional valve 140. Accordingly the feedback control of the depressing force by the pressing device 30 starts to be performed based on the proportional and integral values from step S300.

In step S310, it is determined whether the constant depressing force switch 192 has been switched from ON to OFF by the vehicle operator. If No is obtained, step S300 is repeatedly executed. If Yes is obtained, the process proceeds to step S320 where the control amount for the control command signal is reset to 0. Then, in step S330, the valve position of the master valve 144 is returned to the first position from the second position.

Constant Deceleration Test

Next, a procedure of the constant deceleration test will be described according to the embodiment referring to a flowchart shown in FIG. 12. This constant deceleration test is also started while the vehicle is being driven at a constant vehicle speed by the operator.

In step S410, it is first determined whether the constant deceleration test switch 194 has been switched from OFF to ON by the vehicle operator. If No is obtained, step S410 is repeatedly executed. If Yes is obtained in step S410, the process proceeds to step S420 where the feed-forward gain Kf is set to an initial value (normally 0). Then in step S430, the control signal is output to the master valve 144 such that the valve position of the master valve 144 is switched from the first position to the second position.

In step S440, a signal indicating a target deceleration Gbxt set by the vehicle operator through operation of the target value setting unit 160 is read. In step S440, feed-forward control command signal corresponding to Gbxt·Kf, a product of the target deceleration Gbxt and the feed-forward gain Kf, is output to the electropneumatic proportional valve 140.

In step S450, a signal indicating a longitudinal acceleration Gx detected by the longitudinal acceleration sensor 180 is read. In step S460, it is determined whether reading of the signal indicating the longitudinal acceleration Gx has been performed N2 (a positive constant integer) times. If No is obtained in step S460, the process returns to step S450. If Yes is obtained in step S460, the process proceeds to step S470. The number of times for reading the signal indicating the longitudinal acceleration Gx determined in step S460 is reset to 0 every time the feed-forward gain kf is incremented by ΔKf in step S490 to be described later.

In step S470, an average value Gbxa of deceleration of the vehicle is calculated based on the latest longitudinal acceleration Gx detected N2 times. Then in step S480, it is determined whether the average value Gbxa is greater than R5·Gbxt (R5: positive constant value greater than 0.5 but smaller than 1). If Yes is obtained in step S480, the process proceeds to step S500. If No is obtained in step S480, the process proceeds to step S490 in which the feed-forward gain Kf is incremented by ΔKf, and then returns to step S440.

In step S500, a deviation ΔGbx (=Gbxt−Gbxa) between the target deceleration of the vehicle Gbxt and the average value Gbxa is calculated. In step S500, a control command signal corresponding to a sum of a feed-forward control amount Gbxt·Kf for achieving the target deceleration Gbxt and a proportional control amount Gbx·Kp for the feedback control is output to the electropneumatic proportional valve 140.

In step S510, a signal indicating the longitudinal acceleration Gx of the vehicle detected by the longitudinal acceleration sensor 180 is read. Then in step S520, an average value of the latest deceleration of the vehicle Gbxa detected N3 (a positive constant integer) times is calculated. In step S530, it is determined whether the average value of the deceleration Gbxa is greater than or equal to R6·Gbxt (R6: a positive constant value greater than R5 but smaller than 1). If No is obtained in step S530, the process returns to step S500. If Yes is obtained in step S530, the process proceeds to step S540.

In step S540, a deviation ΔGbt (=Gbxt−Gbxa) between the target deceleration Gbxt and the average value of the deceleration Gbxa is calculated. In step S540, a control command signal corresponding to a sum of the feed-forward control amount Gbxt·kf for achieving the target deceleration Gbxt and a proportional control amount ΔGbx·Kp of the feedback control and an integral control amount ΔGpx·Ki of the feedback control is output to the electropneumatic proportional valve 140.

In step S550, a signal indicating the longitudinal acceleration Gx detected by the longitudinal acceleration sensor 180 is read. Then in step S560, an average value Gbxa of the latest deceleration of the vehicle detected N4 (a positive constant integer) times is calculated.

In step S570, it is determined whether the vehicle is stopped based on the last longitudinal acceleration Gx that has been read out. If No is obtained, the process returns to step S540. If Yes is obtained, the process proceeds to step S580 where the control signal is output to the master valve 144 such that the valve position of the master valve 144 is switched from the second position to the first position. Then the control amount of the control signal to the electropneumatic proportional valve 140 is reset to 0 in step S590.

Test Terminating Control

Figure 14:
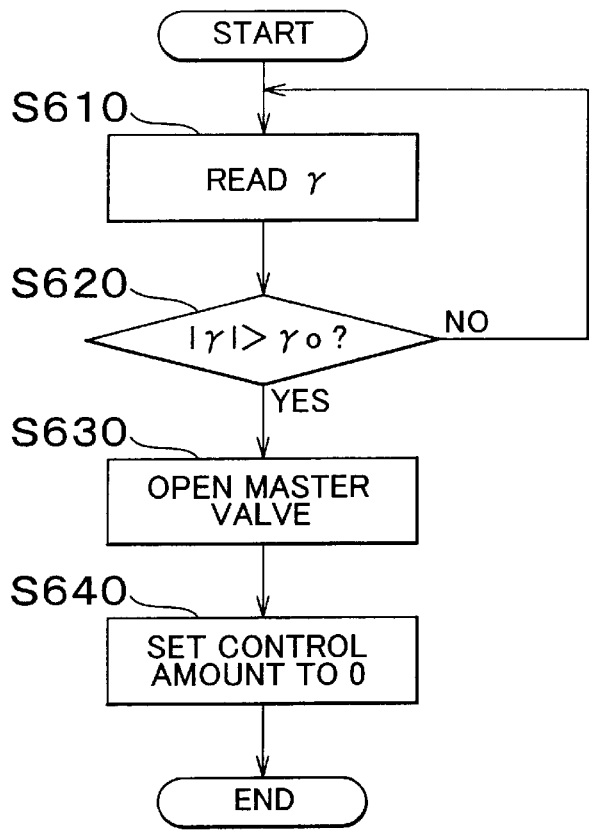
FIG. 14 is a flowchart of a control routine for stopping the test for safety according to the embodiment shown in the figures.

Next, a test terminating control routine for ensuring safety will be described according to the embodiment referring to a flow chart shown in FIG. 14. The control according to the routine shown in FIG. 14 is executed by interrupting the control routines of the flow charts shown in FIGS. 10 and 12, and repeatedly executed at a predetermined interval.

In step S610, a signal indicating a yaw rate γ of the vehicle detected by a yaw rate sensor 186, is read. Then in step S620, it is determined whether an absolute value of the yaw rate is greater than a basic value γ0 (a positive constant value). When No is obtained in step S620, the control according to the control routine shown in the figure ends. If Yes is obtained in step S620, that is, if the vehicle behavior is unstable, the process proceeds to step S630 where the control signal is output to the master valve 144 such that the valve position of the master valve 144 is returned to the first position from the second position. Then in step S640, the control amount of the control signal to the electropneumatic proportion valve 140 is reset to 0, and thereby the first chamber 130 and the second chamber 132 of the pneumatic cylinder/piston device 32 are opened to the ambient air. Accordingly the constant depressing force test or the constant deceleration test is forcibly terminated.

The vehicle operator installs the pressing device 30, turns the main switch 188 ON in the state where the vehicle is stopped, and turns the automatic setting switch 190 such that the value of the feed-forward gain Kf is automatically optimized corresponding to the vehicle subjected to the evaluation test for the braking performance in accordance with the routine shown in FIG. 8. Therefore, the evaluation test can be performed easily and appropriately regardless of a model or type of the vehicle to be tested.

In the embodiment shown in the figures, the vehicle operator turns on the constant depressing force switch 192 while running the vehicle at a predetermined speed in the state where the main switch 188 is turned on after the feed-forward gain Kf has been set. By simply turning the switch 192 off at the completion of the test, the depressing force applied to the brake pedal 10 can be accurately controlled to the target depressing force in accordance with the routine shown in FIG. 10. Therefore, the evaluation test for a braking distance of the vehicle can be performed easily and highly accurately.

In the foregoing embodiment, the vehicle operator turns the constant deceleration switch 194 on while running the vehicle at a predetermined speed in the state where the main switch 188 is turned on after the feed-forward gain Kf has been set. By simply turning on the switch 194, the depressing force applied to the brake pedal 10 can be automatically controlled so as to achieve a predetermined target deceleration accurately in accordance with the routine shown in FIG. 12. Accordingly, the evaluation test for the deceleration of the vehicle can be performed easily and highly accurately.

Particularly, in the constant depressing force test according to the embodiment, the pressing device 30 that applies the pressure to the brake pedal 10 is controlled according to the feed-forward control amount based on the target depressing force Fbpt in steps S240 through S260. Then the pressing device 30 is controlled according to the sum of the feed-forward control amount and the proportional control amount of the feedback control based on the deviation ΔFbp between the target depressing force Fbpt and the depressing force Fbp in steps S270 through S290. Then the pressing device 30 is controlled according to the sum of the feed-forward control amount, the proportional control amount of the feedback control based on the deviation ΔFbp between the target depressing force Fbpt and the depressing force Fbp, and the integral control amount of the feedback control based on an integral value of the deviation ΔFbp between the target depressing force Fbpt and the depressing force Fbp.

The depressing force applied to the brake pedal 10 can be rapidly increased to the target depressing force Fbpt. Concurrently, the depressing force applied to the brake pedal 10 exceeds the target depressing force Fbpt momentarily owing to overshooting. This makes it possible to prevent the depressing force from being smaller than the target depressing force Fbpt, or from fluctuating with respect to the target depressing force Fbpt to a great degree. Therefore, the constant depressing force test can be performed efficiently and accurately.

Figure 15:
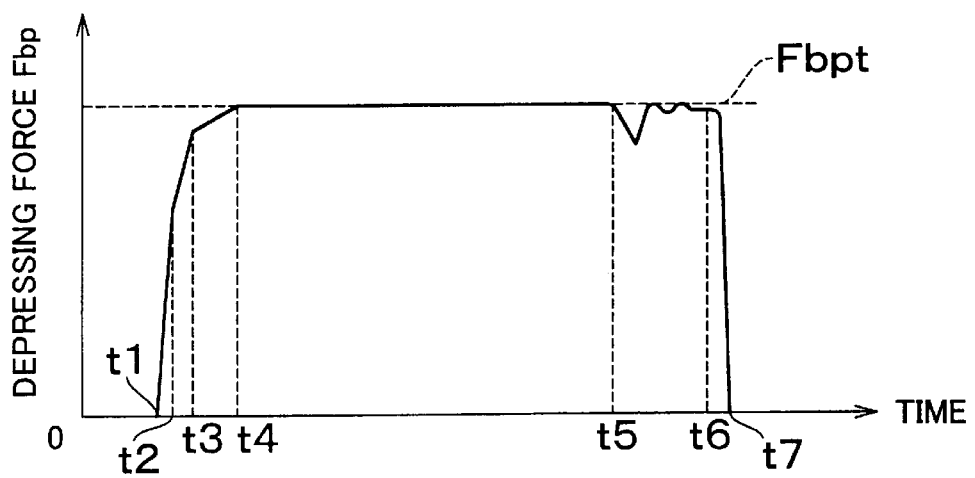
FIG. 15 is a graph representing an example of a change in the pressuring force of the actuator during the constant depressing force test.

Shown in FIG. 15 is one example of a change in the depressing force Fbp during the constant depressing force test, in which the constant depressing force test switch 192 is turned on at a time point t1, and the vehicle is stopped at a time point t5, and the constant depressing force switch 192 is turned off at time point t6.

In this example, the pressing device 30 is controlled according to the feed-forward control amount over a period between time points t1 and t2, rapidly increasing the depressing force Fbp. Following this, it is controlled according to the sum of the feed-forward control amount and the proportional control amount of the feedback control over a period between time points t2 and t3, relatively rapidly increasing the depressing force Fbp, and thereafter, according to the sum of the feed-forward control amount, the proportional control amount of the feedback control, and the integral control amount of the feedback control over a period between time points t3 and t4, gradually increasing the depressing force Fbp until the target depressing force Fbpt has substantially been reached, ensuring the depressing force does not exceed it. Thereafter, the depressing force Fbp, being prevented from deviating in a wide range, is controlled at the target depressing force Fbpt over a period between time points t4 and t5.

The depressing force Fbp fluctuates between time points t5 and t6 due to a backlash generated by an inertia of a vehicle body which arises when the vehicle stops, and, after the first chamber 130 and the second chamber 132 of the pneumatic cylinder/piston device 32 have been opened to the ambient air at time point t6, the depressing force Fbp is thereby reset to 0 in a short period between time points t6 and t7.

According to the embodiment shown in the figures, the pressing device 30 is controlled in the same manner as above during the constant deceleration test to be performed following the routine shown in FIG. 12. First, the pressing device 30, which applies the depressing force to the brake pedal 10, is controlled according to the feed-forward control amount based on the target deceleration Gbxt in steps S440 through S490. Then, it is controlled according to the sum of the feed-forward control amount and the proportional control amount of the feedback control based on the deviation ΔGbx between the target deceleration Gbxt and an actual deceleration of the vehicle Gbxa in steps S500 through S530, and is thereafter controlled according to the sum of the feed-forward control amount, the proportional control amount of the feedback control based on the deviation ΔGbx between the target deceleration Gbxt and an actual deceleration of the vehicle Gbxa, and the integral control amount of the feedback control based on an integral value of the deviation ΔGbx between the target deceleration Gbxt and the actual deceleration of the vehicle Gbxa in steps S540 through S570.

Consequently, the depressing force to be applied to the brake pedal 10 can be appropriately controlled to rapidly bring the actual deceleration of the vehicle to the target deceleration Gbxt. In addition, the depressing force can be surely prevented from temporarily becoming excessive beyond the target deceleration Gbxt due to overshooting at starting the constant depressing force test, and thereafter from becoming smaller than the target depressing force Fbpt, and also deviating in a wide range therefrom. Accordingly, the constant deceleration test can be performed efficiently and accurately.

Further, according to the embodiment shown in the figures, the behavior of the vehicle is evaluated based on yaw rate γ in accordance with the routine shown in FIG. 14 throughout both the constant depressing force test and the constant deceleration test, in which application of the depressing force to the brake pedal 10 by the pressing device 30 is automatically stopped if the behavior of the vehicle is unstable and thereby the constant depressing force test or the constant deceleration test is forcefully terminated to surely prevent the evaluation test from being continued when a running condition of the vehicle is not stable and to thereby improve safety in performing the evaluation test.

According to the embodiment, when the force greater than a predetermined value is applied in a direction where the spherical portion 120 at the tip of the piston rod comes off the hollow 122 of the socket member 108, the pedal-side fixing device 36 disconnects the end of the pneumatic cylinder/piston device 32 from the pedal portion 16 of the brake pedal 10 by elastic or plastic deformation of the holding plate 124. Therefore the vehicle operator is able to stop the vehicle by forcefully pressing the pedal portion 16 to depress the brake pedal 10 in spite of an abnormal state of the pneumatic cylinder/piston device 32 such as a locked state.

Also, in the embodiment, the pneumatic cylinder/piston device 32 serves to generate a pressure applied to the pressing device 30. The first chamber 130 and the second chamber 132 of the pneumatic cylinder/piston device 32 can be momentarily opened to the ambient air by switching the valve positions of the electropneumatic valve 140 and the master valve 144 from the second positions to the first positions, respectively. Therefore the vehicle operator is allowed to stop the test and to operate the brake pedal 10 intentionally by strongly depressing the pedal portion 16 without disconnecting the other end of the pneumatic cylinder/piston device 32 from the pedal portion 16.

In the foregoing embodiment, the pedal-side fixing device 36 is allowed to transmit the depressing force applied by the pneumatic cylinder/piston device 32 to the pedal portion 16 along the axis 110, to align the axis 110 in the direction where the vehicle operator applies the depression force to the pedal portion 16 by means of the pedal abutting portion 92, and to detect the depression force transmitted from the tip of the pneumatic cylinder/piston device 32 to the pedal portion 16 independent from the direction of the pneumatic cylinder/piston device 32 to the pedal surface 16A of the pedal portion. Unlike the case in which the axial force of the pneumatic cylinder-piston device 32 is detected as the depressing force, the depressing force applied to the brake pedal 10 by the pressing device 30 can be accurately detected. Therefore the evaluation test with respect to the braking performance can be accurately conducted.

In the illustrated embodiment, the pedal-side fixing device 36 connects the tip of the pneumatic cylinder/piston device 32 with the pedal portion 16 such that a force can be transmitted in a direction in which the pedal portion 16 is depressed or in the direction opposite thereto. The pneumatic cylinder/piston device 32 is controlled such that the pressure P2 within the second chamber is kept at a substantially constant pressure, and the pressure P1 within the first chamber 130 can be controlled. Therefore, the depressing force applied to the brake pedal 10 can be adjusted for increasing or decreasing with good response. The depressing force applied to the brake pedal 10 can be reduced at the end of the testing of the braking performance.

The invention is not limited to the embodiment described above in detail. It is obvious to a person skilled in the art to which the invention pertains that the invention can be embodied in various forms without departing from the invention.

For example, in the embodiment described above, the depressing force applied by the pressing device 30 is controlled based on the feed-forward control amount, and then controlled based on the sum of the feed-forward control amount and the proportional control amount of the feedback control. The depressing force is further controlled based on the sum of the feed-forward control amount, the proportional control amount of the feedback control and the integral control amount thereof. However, one of the latter two controls, especially the control based on the sum of the feed-forward control amount and the proportional control amount of the feedback control, may be omitted.

Further in the embodiment described above, the pressing device 30 is capable of generating the force in the direction where the depression force is applied to the pedal portion 16 and in the direction opposite thereto. However, the depressing force may be decreased using the return spring 18 installed in the brake pedal 10.

In the embodiment, the constant deceleration test is terminated when it is determined that the vehicle has been stopped based on the longitudinal acceleration Gx of the vehicle detected by the longitudinal acceleration sensor 180. The stop state of the vehicle may be determined based on a vehicle speed detected by a vehicle speed sensor or a person located outside the vehicle. Alternatively the constant deceleration test may be terminated when the constant deceleration test switch 194 is switched from on to off by the vehicle operator.

In the embodiment described above, it is determined whether the behavior of the vehicle is unstable based on the yaw rate γ of the vehicle detected by the yaw rate sensor 186. However, the vehicle behavior may be determined in various other manners known by those skilled in the art.

Steps executed upon termination of the test in the embodiment, that is, steps S190 and S200 shown in FIG. 8, steps S320 and S330 shown in FIG. 10, steps S580 and S590 shown in FIG. 12, and steps S630 and S640 shown in FIG. 14 may be executed in reverse order, respectively.

In the embodiment described above, the pneumatic cylinder/piston device 32 serves to generate the depressing force applied to a control member. The depressing force may be generated by, for example, a hydraulic type cylinder/piston device, an electric device including a rotary driving device such as an electric motor and a converting mechanism such as a ball screw for converting a rotary motion to a linear motion, or an electromagnetic device which electromagnetically generates the depressing force instead of the pneumatic cylinder/piston device 32.

In the embodiment described above, all the load generated along the axis 110 by the pneumatic cylinder/piston device 32 is transmitted to the pedal portion 16 of the brake pedal 10 via the load sensor 106. However, a part of the depressing force generated along the axis 110 may be transmitted to the load sensor 106.

In the embodiment described above, the method and the apparatus according to the invention are applied to the evaluation test for the braking performance of the vehicle. The method and the apparatus may be applied to an accelerator pedal to be pressed by a vehicle operator as an acceleration control, and therefore may be applied to an evaluation test for an acceleration performance of a vehicle.

As is described in detail above, the control to the pressing device 30 is changed in accordance with an actual state of the vehicle. More specifically, the control member is controlled in accordance with the actual state of the vehicle irrespective of the type of the vehicle to be tested such that the control member is depressed. This makes it possible to depress the control member, for example, a brake pedal, irrespective of the change in the test conditions or in the vehicle state, and to conduct the evaluation test with high accuracy.

The actual state of the vehicle is detected, and the pressing device is controlled to bring the vehicle into a predetermined state based on the detected actual state thereof. Hence the pressing device can be surely and appropriately controlled in accordance with the actual state of the vehicle, appropriately depressing the control member.

The actual state of the vehicle is detected, and parameters for controlling the pressing device are changed in accordance with the detected actual state of the vehicle. Hence the pressing device can be surely and appropriately controlled according to the actual state of the vehicle, appropriately depressing the control member.

Since the actual state of the vehicle may be represented by the depressing force applied to the control member by the pressing device, the pressing device is controlled in accordance with the depressing force applied to the control member. Therefore the depressing force applied to the control member can be accurately controlled to achieve a desired depressing force.

Since the actual state of the vehicle may be represented by the deceleration of the vehicle, the pressing device is controlled in accordance with the deceleration of the vehicle. Therefore the depressing force applied to the control member can be accurately controlled to achieve a desired deceleration of the vehicle.

The running condition of the vehicle is detected and, when the running condition of the vehicle is unstable, the depressing force applied to the control member by the pressing device is decreased to terminate the evaluation test for the vehicle performance. Therefore the evaluation test can be surely prevented from being continued when the running condition of the vehicle is not stable.

The control member may be a brake control member, and therefore the evaluation test for the braking performance of the vehicle can be automatically conducted by automatically pressing the brake control member by means of the pressing device.

While the invention has been described with reference to preferred embodiments thereof, it is to be understood that the invention is not limited to the disclosed embodiments or constructions. On the contrary, the invention is intended to cover various modifications and equivalent arrangements. In addition, while the various elements of the disclosed invention are shown in various combinations and configurations, which are exemplary, other combinations and configurations, including more, less or only a single element, are also within the spirit and scope of the invention.

What is claimed is:

1. A method of conducting a performance evaluation test for a vehicle, the method comprising:
   providing an actuator that applies a depressing force to a control member to be operated by a vehicle operator, and a controller that controls the actuator; and
   controlling the actuator to automatically apply the depressing force to the control member for conducting a performance evaluation test for the vehicle;
   wherein controlling the actuator comprises controlling the actuator by:
   a feed-forward control amount obtained on basis of a predetermined state of the vehicle; and then by
   the feed-forward control amount obtained on the basis of the predetermined state of the vehicle, and a feedback control amount on a basis of a deviation between the predetermined state and an actual state of the vehicle.

2. The method according to claim 1, wherein the feedback control amount includes a proportional control amount and a integral control amount.

3. A method of conducting a performance evaluation test for a vehicle, the method comprising:
   providing an actuator that applies a depressing force to a control member to be operated by a vehicle operator, and a controller that controls the actuator; and
   controlling the actuator to automatically apply the depressing force to the control member for conducting a performance evaluation test for the vehicle;
   wherein controlling the actuator comprises controlling the actuator by:
   a feed-forward control amount obtained on a basis of predetermined state of the vehicle; and then by
   the feed-forward control amount obtained on the basis of the predetermined state of the vehicle and a proportional control amount of a feedback control obtained on a basis of a deviation between the predetermined state and an actual state of the vehicle; and then subsequently by the feed-forward control amount obtained on the basis of the predetermined state of the vehicle, and the proportional control amount and an integral control amount of the feedback control obtained on the basis of the deviation between the predetermined state and the actual state of the vehicle.

4. A performance evaluation test apparatus for a vehicle, comprising:

an actuator that presses a control member to be operated by a vehicle operator; and a controller that controls the actuator so as to automatically press the control member for conducting a performance evaluation test for the vehicle;

wherein the actuator is controlled by a feed-forward control amount obtained on a basis of a predetermined state of the vehicle, and the actuator is then controlled by the feed-forward control amount on the basis of the predetermined state of the vehicle, and a feedback control amount on a basis of a deviation between the predetermined state and an actual state of the vehicle.

5. The apparatus according to claim 4, wherein the feedback control amount includes a proportional control amount and an integral control amount.

6. A performance evaluation test apparatus for a vehicle, comprising:

an actuator that presses a control member to be operated by a vehicle operator; and a controller that controls the actuator so as to automatically press the control member for conducting a performance evaluation test for the vehicle:

wherein the actuator is controlled by a feed-forward control amount obtained on a basis of a predetermined state of the vehicle, then the actuator is controlled by the feed-forward control amount obtained on the basis of the predetermined state of the vehicle and a proportional control amount of a feedback control on a basis of a deviation between the predetermined state and an actual state of the vehicle, and subsequently the actuator is controlled by the feed-forward control amount obtained on the basis of the predetermined state of the vehicle, and the proportional control amount and an integral control amount of the feedback control on the basis of the deviation between the predetermined state and the actual state of the vehicle.

* * * * *